United States Patent
Weser et al.

(10) Patent No.: US 9,125,832 B2
(45) Date of Patent: Sep. 8, 2015

(54) COLORING COMPOSITION WITH DIRECT DYES AND ZWITTERIONIC SURFACTANTS

(71) Applicant: Henkel AG & Co. KGaA, Düsseldorf (DE)

(72) Inventors: Gabriele Weser, Neuss (DE); Claudia Kolonko, Remscheid (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 14/310,185

(22) Filed: Jun. 20, 2014

(65) Prior Publication Data

US 2014/0298595 A1    Oct. 9, 2014

Related U.S. Application Data

(63) Continuation of application No. PCT/EP2012/073248, filed on Nov. 21, 2012.

(30) Foreign Application Priority Data

Dec. 20, 2011  (DE) .......................... 10 2011 089 223

(51) Int. Cl.
  *A61Q 5/10*  (2006.01)
  *A61K 8/41*  (2006.01)
  *A61K 8/35*  (2006.01)
  *A61Q 5/06*  (2006.01)
  *A61K 8/44*  (2006.01)

(52) U.S. Cl.
  CPC ................. *A61K 8/416* (2013.01); *A61K 8/355* (2013.01); *A61K 8/44* (2013.01); *A61Q 5/065* (2013.01); *A61Q 5/10* (2013.01)

(58) Field of Classification Search
  CPC ......... A61Q 5/10; A61Q 5/065; A61K 8/355; A61K 8/416; A61K 8/411
  USPC .............. 8/405, 426, 454, 455, 580, 582, 643
  See application file for complete search history.

(56) References Cited

U.S. PATENT DOCUMENTS

| | | | | |
|---|---|---|---|---|
| 8,298,296 B2 * | 10/2012 | Wood et al. | ....................... | 8/405 |
| 2008/0313820 A1 | 12/2008 | Huet et al. | | |
| 2013/0156716 A1 * | 6/2013 | Yontz | ........................... | 424/70.6 |

FOREIGN PATENT DOCUMENTS

| | | | | |
|---|---|---|---|---|
| CA | 2613049 | * | 4/2008 | ............... A61Q 5/10 |
| CA | 2613049 A1 | | 4/2008 | |
| EP | 0137178 A2 | | 4/1985 | |
| EP | 1006154 B1 | | 6/2000 | |
| EP | 1820826 A1 | | 8/2007 | |
| EP | 2329809 A1 | | 6/2011 | |

OTHER PUBLICATIONS

STIC Search Report dated Aug. 25, 2014.*

* cited by examiner

*Primary Examiner* — Eisa Elhilo
(74) *Attorney, Agent, or Firm* — Steven L. Nichols; Van Cott, Bagley, Cornwall & McCarthy P.C.

(57) ABSTRACT

Agents for coloring keratinic fibers, containing (a) at least one compound of formula (I), and (b) at least one zwitterionic surfactant are disclosed and described.

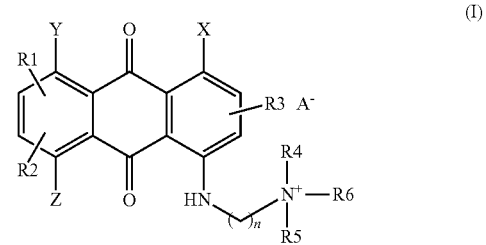

20 Claims, No Drawings

COLORING COMPOSITION WITH DIRECT DYES AND ZWITTERIONIC SURFACTANTS

RELATED DOCUMENTS

The present application claims the benefit and is a U.S. continuation patent application under 35 U.S.C. 111(a) and claims the right of priority under 35 U.S.C. 365 to international patent Application No. PCT/EP2012/073248, filed Nov. 21, 2012, entitled "COLORING COMPOSITION WITH DIRECT DYES AND ZWITTERIONIC SURFACTANTS" which claims benefit of German application No.: 102011089223.0, filed Dec. 20, 2011, these applications are herein incorporated by reference in their entirety.

FIELD OF THE INVENTION

The present application generally relates to agents for coloring and optionally lightening keratinic fibers, in particular human hair, containing specific cationic anthraquinone dyes and zwitterionic surfactants. The application also generally relates to the use of these agents to produce hair colors having increased shine, an intense color result, improved fastness properties and reduced selectivity.

BACKGROUND OF THE INVENTION

Generally, either substantive dyes or oxidation dyes are used for coloring keratinic fibers. Although intense colors with good fastness properties can be obtained with oxidation dyes, the development of the color generally takes place under the influence of oxidizing agents such as $H_2O_2$ for example, which in some cases can damage the fiber. Furthermore, some oxidation dye precursors or certain mixtures of oxidation dye precursors can have a sensitizing effect on people with sensitive skin. Substantive dyes are typically applied under gentler conditions. The disadvantage of these dyes, however, is that the colors often have inadequate fastness properties, in particular regard to hair washing, but also in respect to external influences like sunlight, or reactive environmental chemicals like swimming pool water. Such colors are also generally significantly more sensitive to shampooing than oxidative colors, so that an often undesired shift in shade or even a visible "decolorization" occurs much more quickly.

Achieving a uniform coloring of frequently pretreated hair, for example bleached or permanently waved hair, where the fibers present differing degrees of pre-damage, represents a particular challenge in terms of coloring hair with substantive dyes. During the coloring process itself, the coloring agent can exhibit an uneven coloring behavior on differently pre-damaged hair. Repeated hair washing can also cause the dyes to be washed out of the different areas of the hair to varying degrees, resulting in an inconsistent and undesirable color result.

In the development of coloring products based on substantive dyes, there is a particular focus on producing dye formulations having reduced selectivity, in order to achieve a uniform color result on sections of the hair that are damaged to varying degrees. In particular, this reduced selectivity should still be present not only immediately after the coloring process but also after repeated hair washes.

BRIEF SUMMARY OF THE INVENTION

The present application provides a coloring agent (i.e. composition) for keratinic fibers, in particular human hair, which, in addition to other positive fastness properties, has a low selectivity (or a good equalizing capacity) and good wash fastness.

The colors achieved with the agents according to the invention deliver a brilliant and intense color result, both immediately after the coloring process, and after repeated hair washes. Following application of the coloring agent the hair can desirably be uniformly colored, even in cases where the hair is damaged to varying degrees, wherein this uniformity in the color result should still be present even after repeated hair washes. In particular, brilliant and neutral blue shades or shades in the blue region with the advantageous fastness properties described above should be achieved, said shades also being outstandingly suitable for matting. The agents should additionally can desirably have an optimized viscosity in terms of both the application process and the coloring capacity.

DETAILED DESCRIPTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The use of cationic anthraquinone dyes in products for coloring keratinic fibers is already known in principle from the prior art, for example from EP 1006154 or EP1820826. Furthermore, combinations of cationic anthraquinone dyes with oxidation dye precursors of the developer type are claimed in EP2329809 for the oxidative coloring of hair.

Surprisingly, it has been found that combinations of specific cationic anthraquinones as substantive dyes with zwitterionic surfactants lead to colors which achieve the desired keratinic fiber coloring results to an outstanding degree.

Combinations of the specific cationic anthraquinones according to the first subject matter disclosed herein with zwitterionic surfactants have not yet been described in the prior art.

The present specification firstly provides an agent for coloring and optionally lightening keratinic fibers, in particular human hair, wherein the agent contains in a cosmetic carrier (a) a compound of formula (I)

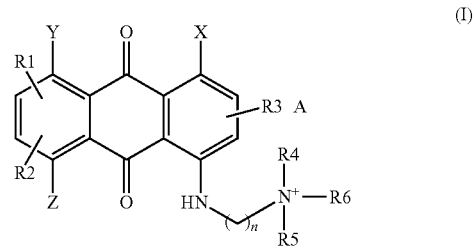

wherein the R1, the R2, and the R3 each independently of one another denote a hydrogen, a halogen, a nitro group, a cyano group, a carboxyl group, a sulfonic acid group, a hydroxyl group, a $C_1$-$C_6$ acyl amino group, a carboxamide group, a sulfonamide group, a $C_1$-$C_6$ alkyl group, $C_1$-$C_6$ alkoxy group, a $C_2$-$C_6$ alkenyl group, a $C_2$-$C_6$ hydroxyalkyl group, or a $C_1$-$C_6$ alkoxy $C_2$-$C_6$ alkyl group;

the R4, the R5, and the R6 each independently of one another denote a $C_1$-$C_6$ alkyl group, a $C_2$-$C_6$ alkenyl group, a $C_2$-$C_6$ hydroxyalkyl group, or a $C_1$-$C_6$ alkoxy $C_2$-$C_6$ alkyl group;

the X, the Y, and the Z each independently of one another denote a hydrogen or an N(R7)(R8) group, wherein the R7 and the R8 each independently of one another denote a hydrogen, a $C_1$-$C_6$ alkyl group, a $C_2$-$C_6$ alkenyl group, a $C_2$-$C_6$ hydroxyalkyl group, or a $C_1$-$C_6$ alkoxy $C_2$-$C_6$ alkyl group, and that at least one of the residues X, Y and Z denotes an N(R7)(R8) group;

the n denotes a number from 2 to 6;

the $A^-$ denotes a physiologically acceptable anion; and (b) a zwitterionic surfactant.

The term "keratinic fibers" or "keratin fibers" may be used interchangeably and is understood to mean fur, wool, feathers and in particular human hair. Although the agents according to the invention are primarily suitable for coloring keratin fibers, there is nothing in principle to preclude their use in other fields.

The term "coloring keratin fibers" used according to the invention includes any form of color changing of fibers. It includes in particular the color changes covered by the terms tinting, lightening, bleaching, peroxiding, oxidative coloring, semipermanent coloring, permanent coloring and temporary coloring. It explicitly also includes color changes according to the invention presenting a lighter color result in comparison to the original color, such as for example coloring bleaching processes.

The agents (i.e. compositions) contain the active agents in a cosmetic carrier, preferably in a suitable aqueous, alcoholic or aqueous-alcoholic carrier. For the purposes of hair coloring such carriers include, for example, creams, emulsions, gels or surfactant-containing foaming solutions, such as shampoos, foam aerosols, foam formulations or other preparations which are suitable for use on the hair. It is also possible, however, for the agents according to the invention to be integrated into a formulation in powder or tablet form.

Within the meaning of the present specification aqueous-alcoholic solutions are understood to be aqueous solutions containing 3 to 70 wt. % of a $C_1$ to $C_4$ alcohol, in particular ethanol or isopropanol. The agents according to the invention can additionally contain further organic solvents, such as for example methoxybutanol, benzyl alcohol, ethyl diglycol or 1,2-propylene glycol. All water-soluble organic solvents are preferred here. An aqueous carrier contains within the meaning of the invention at least 30 wt. %, in particular at least 50 wt. % of water, relative to the total weight of the agent. Aqueous carriers are preferred according to the invention such that the agent has a proportion of at least 80 wt. %, preferably at least 85 wt. %, relative to the total weight of the agent.

As the first ingredient (a) the agents contain at least one substantive cationic anthraquinone dye of general formula (I).

The substituents R1 to R8 of the compound of formula (I) are described below by way of example: Examples of a $C_1$-$C_6$ alkyl group are the methyl, ethyl, propyl, isopropyl, n-butyl, s-butyl and t-butyl, n-pentyl and n-hexyl groups. Propyl, ethyl and methyl are preferred alkyl residues. Examples of a $C_2$-$C_6$ alkenyl group are vinyl, allyl, but-2-enyl, but-3-enyl and isobutenyl, preferred $C_2$-$C_6$ alkenyl residues being vinyl and allyl. Preferred examples of a $C_1$-$C_6$ hydroxyalkyl group are a hydroxymethyl, 2-hydroxyethyl, 2-hydroxypropyl, 3-hydroxypropyl, 4-hydroxybutyl, 5-hydroxypentyl and 6-hydroxyhexyl group; a 2-hydroxyethyl group is particularly preferred. $C_1$-$C_6$ alkoxy groups that are preferred according to the invention are the methoxy or ethoxy group. Examples of halogen atoms are F, Cl, Br or I atoms, with Br or Cl atoms being most particularly preferred. Preferred examples of $C_1$-$C_6$ alkoxy $C_2$-$C_6$ alkyl groups according to the invention are the methoxyethyl, ethoxyethyl, methoxypropyl, methoxybutyl, ethoxypropyl, ethoxybutyl and methoxyhexyl group. Examples of a $C_1$-$C_6$ acyl amino group are the acetamide group, the propanamide group and the butanamide group, the acetamide group being preferred. The pyrrolidinium ring, the piperidinium ring, the morpholinium ring and the 1-azepanium ring can be mentioned as preferred examples of a 5-, 6- or 7-membered ring formed from R4, R5 and the quaternary nitrogen atom.

Dyes of formula (I) in which R1, R2 and R3 independently of one another denote a hydrogen, a halogen, a carboxyl group, a sulfonic acid group, a $C_1$-$C_6$ alkyl group or a $C_1$-$C_6$ alkoxy group deliver particularly intense color results and are therefore preferred.

It is furthermore preferable for one of the residues selected from R1, R2 and R3 to denote a halogen, a carboxyl group, a sulfonic acid group, a $C_1$-$C_6$ alkyl group or a $C_1$-$C_6$ alkoxy group and for the other two residues selected from R1, R2 and R3 both to denote hydrogen.

A preferred embodiment of the first subject matter of the invention is an agent for coloring and optionally lightening keratinic fibers, comprising a compound of formula (I) in which at least one of the residues R1, R2 and/or R3 denotes a $C_1$-$C_6$ alkyl group.

In the case of particularly suitable compounds of formula (I), one of the residues selected from R1, R2 and R3 denotes a $C_1$-$C_6$ alkyl group and the other two residues selected from R1, R2 and R3 denote hydrogen.

In an explicitly most particularly preferred embodiment R1 and R2 both denote a hydrogen atom and R3 denotes a methyl group.

Furthermore, particularly good coloring results can be obtained using agents comprising at least one compound of formula (I) in which the residues R4, R5 and R6 independently of one another denote a $C_1$-$C_6$ alkyl group or an alkenyl group. In particular, each of the residues R4, R5 and R6 preferably denotes a $C_1$-$C_6$ alkyl group.

It is most particularly preferable for R4 and R5 both to denote a methyl group and for R6 to denote a methyl group, an ethyl group, or an n-propyl group.

It is moreover most particularly preferable for R4 and R5 both to denote a methyl group and for R6 to denote an n-propyl group.

In a likewise particularly preferred embodiment the residues R4, R5 and R6 each denote a methyl group.

For compounds of formula (I) there is the proviso that at least one of the residues X, Y and Z denote an N(R7)(R8) group. Colors having good application properties were obtained when compounds of formula (I) were used in which X denotes an N(R7)(R8) group and Y and Z each denote hydrogen.

In one embodiment, R7 and R8 preferably independently of one another denote hydrogen or a $C_1$-$C_6$ alkyl group. R7 and R8 particularly preferably independently of one another denote hydrogen or a methyl group. Compounds of formula (I) in which both R7 and R8 denote hydrogen have proved to be particularly suitable and are therefore particularly preferred.

In the context of the work leading to this invention it has proved most particularly advantageous for X to denote an $NH_2$ group.

A further preferred embodiment is therefore an agent for coloring and optionally lightening keratinic fibers, comprising a compound of formula (I) in which at least X denotes an NH₂ group.

In one embodiment, n preferably denotes the numbers 2 or 3 and most particularly preferably the number 3.

In another embodiment, A⁻ denotes a physiologically acceptable anion. Suitable physiologically acceptable anions include halide, hydrogen sulfate, sulfate, benzenesulfonate, p-toluenesulfonate, acetate, citrate, lactate, tartrate, methyl sulfate ($H_3COSO_3^-$), methyl sulfonate or trifluoromethane sulfonate. A⁻ particularly preferably denotes bromide or methyl sulfate ($H_3COSO_3^-$), with A⁻ most particularly preferably denoting methyl sulfate ($H_3COSO_3^-$).

Agents for coloring and optionally simultaneously lightening keratinic fibers that are preferred according to the invention are characterized in that they contain at least one compound of general formula (I) selected from 3-[(4-amino-9,10-dihydro-3-methyl-9,10-dioxo-1-anthracenyl)amino]-N,N,N-trimethyl-1-propanaminium methyl sulfate, 3-[(4-amino-9,10-dihydro-3-methyl-9,10-dioxo-1-anthracenyl)amino]-N,N,N-trimethyl-1-propanaminium bromide, 3-[(4-amino-9,10-dihydro-3-methyl-9,10-dioxo-1-anthracenyl)amino]-N,N,N-trimethyl-1-propanaminium chloride, 3-[(4-amino-9,10-dihydro-3-methyl-9,10-dioxo-1-anthracenyl)amino]-N,N,N-trimethyl-1-propanaminium-p-toluenesulfonate, 3-[(4-amino-9,10-dihydro-3-methyl-9,10-dioxo-1-anthracenyl)amino]-N,N,N-trimethyl-1-propanaminium acetate, 3-{[9,10-dihydro-4-(methylamino)-9,10-dioxo-1-anthracenyl]amino}-N,N-dimethyl-N-propyl-1-propanaminium methyl sulfate, 3-{[9,10-dihydro-4-(methylamino)-9,10-dioxo-1-anthracenyl]amino}-N,N-dimethyl-N-propyl-1-propanaminium bromide, 3-{[9,10-dihydro-4-(methylamino)-9,10-dioxo-1-anthracenyl]amino}-N,N-dimethyl-N-propyl-1-propanaminium chloride, 3-{[9,10-dihydro-4-(methylamino)-9,10-dioxo-1-anthracenyl]amino}-N,N-dimethyl-N-propyl-1-propanaminium-p-toluenesulfonate and 3-{[9,10-dihydro-4-(methylamino)-9,10-dioxo-1-anthracenyl]amino}-N,N-dimethyl-N-propyl-1-propanaminium acetate.

The compound of the formula (Ia) was ideally suitable for achieving the desired results,

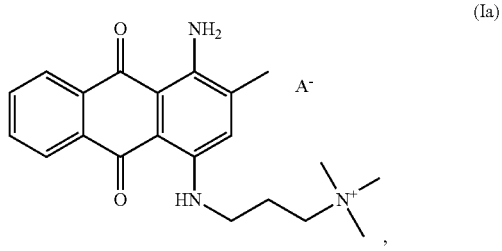

(Ia)

in which A⁻ denotes a physiologically acceptable anion, preferably methyl sulfate ($H_3COSO_3^-$). The compound (Ia) in which A⁻ denotes methyl sulfate is also known under the name Cationic Blue 347.

A further particularly preferred embodiment is therefore an agent for coloring and optionally lightening keratinic fibers, which is characterized in that it contains as the compound of formula (I) a compound according to formula (Ia),

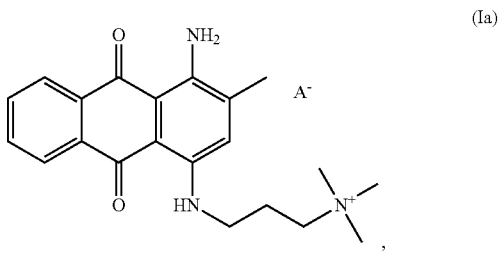

(Ia)

in which A⁻ denotes a physiologically acceptable anion, preferably methyl sulfate ($H_3COSO_3^-$).

The agents according to the present technology for coloring and optionally simultaneously lightening keratin fibers include the compound(s) of formula (I) preferably in amounts above 0.0001 wt. % and below 5 wt. %, relative in each case to the total agent.

A further preferred embodiment is an agent which contains the compound(s) of formula (I) in a proportion from 0.0001 to 5 wt. %, preferably 0.005 to 3.5 wt. %, particularly preferably 0.01 to 2.5 wt. %, in particular 0.05 to 1.5 wt. %, and in particular preferably from 0.01 to 1.0 wt. %, relative in each case to the total weight of the agent.

As the second constituent of the formulation (b) the agents include at least one zwitterionic surfactant.

The term "zwitterionic surfactant" refers to compounds which have a hydrophobic molecule part comprising mostly long-chain alkyl residues, and also having a hydrophilic part, wherein the hydrophilic part is an internal salt. The positive charge of the internal salt is preferably represented by a quaternary ammonium salt, while the anionic charge is preferably derived from a carboxylate or sulfonate.

$C_6$-$C_{24}$ alkyl residues, which can be saturated or unsaturated and optionally branched, are preferably used as the hydrophobic part. Depending on the source and production, it is preferable to use a mixture of compounds having differing alkyl chain lengths as the zwitterionic surfactant.

In addition to the hydrophobic part and the residue bearing the anionic charge, a quaternary ammonium ion also bears two further substituents, which are preferably selected from $C_1$-$C_6$ alkyl residues or $C_2$-$C_6$ hydroxyalkyl residues.

Preferred zwitterionic surfactants are (i) $C_6$-$C_{24}$ acylaminoalkyl(di-$C_1$-$C_6$ alkyl)ammonioglycinates, ($C_6$-$C_{24}$ acylaminoalkyl)($C_2$-$C_6$ hydroxyalkyl)($C_1$-$C_6$ alkyl)ammonioglycinates, $C_6$-$C_{24}$ acylaminoalkyl di($C_2$-$C_6$ hydroxyalkyl)ammonioglycinates;

Examples are in particular the compounds with the INCI names Capryl/Capramidopropyl Betaine, Cocamidopropyl Betaine, Lauramidopropyl Betaine, Soyamidopropyl Betaine as well as Stearamidopropyl Betaine, Cetamidopropyl Betaine, Cetearamidopropyl Betaine, Behenamidopropyl Betaine and Oleamidopropyl Betaine.

(ii) $C_6$-$C_{24}$ alkyl(di-$C_1$-$C_6$ alkyl)ammonioglycinates, ($C_6$-$C_{24}$ alkyl)($C_2$-$C_6$-hydroxyalkyl)($C_1$-$C_6$ alkyl)ammonioglycinates, $C_6$-$C_{24}$ alkyl di($C_2$-$C_6$ hydroxyalkyl)ammonioglycinates. Examples are in particular the compounds with the INCI names Lauryl Betaine, Cetyl Betaine and Coco Betaine, Dihydroxyethyl Stearyl Glycinate (=Bis(Hydroxyethyl) Stearyl Betaine), Bis(Hydroxyethyl) Tallow Alkyl Betaine, as well as Caprylyl Betaine, Capryl Betaine, Soyalkyl Betaine, Stearyl Betaine, Cetearyl Betaine, Behenyl Betaine and Oleyl Betaine.

(iii) $C_6$-$C_{24}$ acylaminoalkyl(di-$C_1$-$C_6$ alkyl)ammonioalkyl sulfonates, ($C_6$-$C_{24}$ acylaminoalkyl)($C_2$-$C_6$ hydroxyalkyl) ($C_1$-$C_6$ alkyl)ammonioalkyl sulfonates, $C_6$-$C_{24}$ acylaminoalkyl di($C_2$-$C_6$ hydroxyalkyl)ammonioalkyl sulfonates;
Examples are in particular the compounds 3-[(Lauramidoethyl)dimethylammonio]-2-hydroxypropanesulfonate, 3-[(Lauramidoethyl)dimethylammonio]propanesulfonate, 3-[(Cocamidoethyl)dimethylammonio]-2-hydroxypropanesulfonate, 3-[(Cocamidoethyl)dimethylammonio]propanesulfonate, 3-[(Stearamidoethyl)dimethylammonio]-2-hydroxypropanesulfonate and 3-[(Stearamidoethyl)dimethylammonio]propanesulfonate.

(iv) $C_6$-$C_{24}$ alkyl(di-$C_1$-$C_6$ alkyl)ammonioalkyl sulfonates, ($C_6$-$C_{24}$ alkyl)($C_2$-$C_6$ hydroxyalkyl)($C_1$-$C_6$ alkyl)ammonioalkyl sulfonates, $C_6$-$C_{24}$ alkyl di($C_2$-$C_6$ hydroxyalkyl)ammonioalkyl sulfonates.

Examples are in particular the compounds 3-[(Lauryl)dimethylammonio]-2-hydroxypropanesulfonate, 3-[(Lauryl)dimethylammonio]propanesulfonate, 3-[(Cocoyl)dimethylammonio]-2-hydroxypropanesulfonate, 3-[(Cocoyl)dimethylammonio]propanesulfonate, 3-[(Stearyl)dimethylammonio]-2-hydroxypropanesulfonate and 3-[(Stearyl)dimethylammonio]propanesulfonate.

Alkylamidopropyldimethyl betaines and/or alkyldimethyl betaines have proved to be particularly advantageous with respect to color uptake.

A further embodiment of the first subject matter of the present technology is an agent wherein the zwitterionic surfactant comprises at least one of alkylamidopropyldimethyl betaine and/or alkyldimethyl betaine.

Most particularly, advantageous results with respect to color uptake and care effect on the fibers can be obtained with Cocamidopropyl Betaine (N-cocoalkylamidopropyl)-N,N-dimethylammonioglycinate).

A further embodiment of the first subject matter of the present technology is an agent comprising Cocamidopropyl Betaine as the zwitterionic surfactant.

The zwitterionic surfactants are preferably present in the agent in a proportion which ensures an optimum care performance on the hair, which correspondingly supports the solubility or emulsifiability of further ingredients and which adjusts the viscosity of the agents. At the same time, the content of zwitterionic surfactants should be kept as low as possible to save on raw materials and to guard against excessive degreasing of the scalp.

A further embodiment of the first subject matter of the present technology is therefore an agent the zwitterionic surfactant(s) comprises a proportion from 0.001 to 15 wt. %, preferably 0.005 to 8 wt. %, particularly preferably 0.01 to 5.0 wt. %, in particular 0.05 to 3.0 wt. %, and in particular preferably from 0.1 to 2.0 wt. %, relative in each case to the total weight of the agent.

In a further preferred embodiment the agents further comprise, at least one further substantive dye. Substantive dyes can be divided into anionic, cationic and non-ionic substantive dyes. The substantive dyes are preferably selected from nitrophenylenediamines, nitroaminophenols, azo dyes, anthraquinones, triarylmethane dyes or indophenols and physiologically acceptable salts thereof. The additional substantive dyes are each preferably used in a proportion from 0.001 to 2 wt. %, relative to the total application preparation.

Preferred anionic substantive dyes include the compounds known under the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue.

Preferred cationic substantive dyes include cationic triphenylmethane dyes, such as for example Basic Blue 7, Basic Blue 26, Basic Violet 2 and Basic Violet 14, aromatic systems which are substituted with a quaternary nitrogen group, such as for example Basic Yellow 57, Basic Red 76, Basic Blue 99, Basic Brown 16 and Basic Brown 17, as well as substantive dyes containing a heterocyclic compound having at least one quaternary nitrogen atom, in particular Basic Yellow 87, Basic Orange 31 and Basic Red 51. The cationic substantive dyes sold under the Arianor trademark are likewise preferred cationic substantive dyes according to the invention.

Non-ionic nitro and quinone dyes and neutral azo dyes in particular are suitable as non-ionic substantive dyes. Preferred non-ionic substantive dyes include the compounds known under the international names or trade names HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol.

Coloring results with outstanding color intensity, brilliance and good wash fastness can be obtained in particular if the agent further comprises a substantive dye selected from D&C Red No. 33 (Acid Red 33), Acid Black No. 1, D&C Orange No. 4 (Acid Orange No. 4), Acid Red 18, Basic Red 76, Acid Violet 43, HC Blue No. 12, N-(2-hydroxyethyl)-4-methyl-2-nitroaniline (Methyl Yellow), HC Yellow No. 2, Red B 54 and 2-amino-6-chloro-4-phenol.

It is not necessary for the optionally included substantive dyes each to be uniform compounds. Instead it is possible for them also to contain small amounts of further components arising from the manufacturing processes for the individual dyes, provided that they do not adversely influence the coloring result or need to be excluded for other, for example toxicological, reasons.

The agents can moreover also be used as oxidation coloring agents. Such oxidation coloring agents additionally contain at least one oxidation dye precursor, preferably at least one oxidation dye precursor of the developer type and at least one oxidation dye precursor of the coupler type. Particularly suitable oxidation dye precursors of the developer type are selected from at least one compound from the group comprising p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one and the physiologically acceptable salts thereof.

Particularly suitable oxidation dye precursors of the coupler type are selected from the group comprising 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically acceptable salts thereof.

The substantive dyes, developer components, and coupler components are preferably each used in an amount from 0.0001 to 5.0 wt. %, preferably 0.001 to 2.5 wt. %, relative in each case to the ready-to-use agent. Developer components and coupler components are generally used in approximately molar amounts to one another. Although the molar use has proved convenient, a certain excess of individual oxidation dye precursors is not disadvantageous, such that developer components and coupler components can be in a molar ratio of 1 to 0.5 to 1 to 3, in particular 1 to 1 to 1 to 2.

In the case of oxidation coloring agents the agents preferably contain an oxidizing agent, preferably hydrogen peroxide. The amounts of hydrogen peroxide correspond to the amounts in the lightening agents according to the invention.

The agents can moreover be used as lightening coloring agents. In order to achieve the lightening effect the agents contain hydrogen peroxide and/or one of the solid addition products thereof with organic or inorganic compounds.

A further embodiment of the first subject matter further comprises hydrogen peroxide and/or one of the solid addition products thereof with organic or inorganic compounds.

In a preferred embodiment, hydrogen peroxide itself is preferably used as an aqueous solution. The concentration of a hydrogen peroxide solution in the agent is determined by legal requirements and the desired effect; 6 to 12 wt. % solutions in water are preferably used. Ready-to-use agents of a preferred embodiment comprise, relative to the total weight of the ready-to-use agent, 0.5 to 20 wt. %, preferably 1 to 12.5 wt. %, particularly preferably 2.5 to 10 wt. % and in particular 3 to 6 wt. % of hydrogen peroxide, relative in each case to the total weight of the agent.

In order to achieve a stronger lightening and bleaching effect the agent can moreover contain at least one peroxo salt.

Suitable peroxo salts include inorganic peroxo compounds, preferably selected from the group formed from ammonium peroxodisulfate, alkali metal peroxodisulfates, ammonium peroxomonosulfate, alkali metal peroxomonosulfates, alkali metal peroxodiphosphates and alkaline-earth metal peroxides. Peroxodisulfates are particularly preferred, in particular ammonium peroxodisulfate, potassium peroxodisulfate and sodium peroxodisulfate.

The persulfates are each included in the agent in an amount from 0.5 to 20 wt. %, preferably 1 to 12.5 wt. %, particularly preferably 2.5 to 10 wt. % and in particular 3 to 6 wt. %, relative to the total weight of the ready-to-use agent.

A further preferred embodiment is an agent for coloring and optionally lightening keratinic fibers, which further comprises hydrogen peroxide, one of the solid addition products thereof with organic or inorganic compounds, ammonium peroxodisulfate, potassium peroxodisulfate and/or sodium peroxodisulfate, each in an amount from 0.5 to 20 wt. %, preferably 1 to 12.5 wt. %, particularly preferably 2.5 to 10 wt. % and in particular 3 to 6 wt. %, relative to the total weight of the ready-to-use agent.

To strengthen the bleaching effect the agent can contain further bleaching strength intensifiers, such as for example tetraacetyl ethylene diamine (TAED), 1,5-diacetyl-2,4-dioxohexahydro-1,3,5-triazine (DADHT), tetraacetyl glycoluril (TAGU), N-nonanoyl succinimide (NOSI), n-nonanoyl or isononanoyl oxybenzene sulfonate (n- or i-NOBS), phthalic acid anhydride, triacetin, ethylene glycol diacetate and 2,5-diacetoxy-2,5-dihydrofuran as well as carbonate salts or hydrogen carbonate salts, in particular ammonium hydrogen carbonate, ammonium carbonate, sodium hydrogen carbonate, disodium carbonate, potassium hydrogen carbonate, dipotassium carbonate and calcium carbonate, and nitrogen-containing, heterocyclic bleaching strength intensifiers, such as 4-acetyl-1-methylpyridinium-p-toluenesulfonate, 2-acetyl-1-methylpyridinium-p-toluenesulfonate as well as N-methyl-3,4-dihydroisoquinolinium-p-toluenesulfonate.

To further increase the lightening, at least one $SiO_2$ compound such as silicic acid or silicates, in particular water glasses, can additionally be added to the composition according to the invention. It can be preferable according to the invention to use the $SiO_2$ compounds in amounts from 0.05 wt. % to 15 wt. %, particularly preferably in amounts from 0.15 wt. % to 10 wt. % and most particularly preferably in amounts from 0.2 wt. % to 5 wt. %, relative in each case to the anhydrous composition. The specified amounts indicate the content of $SiO_2$ compounds (excluding their water component) in the agents.

The ready-to-use coloring agents can moreover contain additional active agents, auxiliary substances and additives to improve the coloring capacity and to establish further desired properties of the agents.

The ready-to-use coloring agents are preferably provided as a liquid preparation and therefore a further surface-active substance is additionally added to the agents, the surface-active substances being referred to as surfactants or emulsifiers, depending on the field of application. They are preferably selected from anionic, cationic, non-ionic and amphoteric surfactants and emulsifiers.

Agents that are preferred comprise at least one anionic surfactant. Preferred anionic surfactants include fatty acids, alkyl sulfates, alkyl ether sulfates and ether carboxylic acids with 10 to 20 C atoms in the alkyl group and up to 16 glycol ether groups in the molecule. The anionic surfactants are used in proportions from 0.1 to 45 wt. %, preferably 1 to 30 wt. % and most particularly preferably from 1 to 15 wt. %, relative to the total amount of the ready-to-use agent.

Addition products of ethylene oxide and/or propylene oxide with fatty alcohols, fatty acids, fatty acid amides, polyol esters of fatty acids and polyol ethers of fatty alcohols, as well as alkyl polyglucosides are suitable in particular as non-ionic surfactants. Examples of suitable non-ionic surfactants are Laureth-2, Beheneth-10, Ceteareth-12, Trideceth-12, Oleth-16, Ceteareth-20, Ceteareth-30 and Ceteareth-50 as well as PPG-1 Trideceth-6, PEG-7 oleate, PEG-90 stearate, PEG-30 cocoate, Polysorbate-20, Polysorbate-60, Polysorbate-65, Polysorbate-80, Polysorbate-85, lauryl glucoside, decyl glucoside and/or coco glucoside.

Agents that are preferred further comprise at least one amphoteric surfactant. Preferred amphoteric surfactants include N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids. Particularly preferred amphoteric surfactants include N-cocoalkyl aminopropionate, cocoacylaminoethyl aminopropionate and $C_{12}$-$C_{18}$ acyl sarcosine.

The non-ionic or amphoteric surfactants are used in proportions from 0.01 to 45 wt. %, preferably 0.1 to 30 wt. % and most particularly preferably from 1 to 15 wt. %, relative to the total amount of the ready-to-use agents.

Agents that are suitable for use can also contain cationic surfactants of the quaternary ammonium compound, esterquat and amidoamine type. Preferred quaternary ammonium compounds are ammonium halides and the imidazolium compounds known under the INCI names Quaternium-27 and Quaternium-83. Further cationic surfactants which can be used according to the invention are the quaternized protein hydrolysates. A compound from the amidoamines that is particularly suitable according to the invention is the stearamidopropyl dimethylamine which is commercially available under the name Tegoamid® S 18. Preferred esterquats are quaternized ester salts of fatty acids with triethanolamine, quaternized ester salts of fatty acids with diethanol alkyl amines and quaternized ester salts of fatty acids with 1,2-dihydroxypropyl dialkylamines. The cationic surfactants preferably comprise proportions from 0.05 to 10 wt. %, relative to the total agent.

The ready-to-use agents can contain further auxiliary substances and additives. Thus it has proved advantageous if the agents contain at least one thickening agent. There are no restrictions in principle regarding these thickening agents. Both organic and also purely inorganic thickening agents can be used.

Suitable thickening agents include
cationic, synthetic polymers;
anionic, synthetic polymers, such as polyacrylates, acrylates copolymer, copolymers of acrylic acid and methacrylic acid;
naturally occurring thickening agents, such as non-ionic guar gums, scleroglucan gums or gum arabic, ghatti gum, karaya gum, tragacanth gum, carrageen gum, carob seed meal, pectins, xanthan gums, alginates, starch fractions and derivatives such as amylose, amylopectin and dextrins, as well as cellulose derivatives, such as for example carboxymethyl cellulose, methyl cellulose and hydroxyalkyl celluloses;
non-ionic, fully synthetic polymers, such as polyvinyl alcohol or polyvinylpyrrolidinone; and
inorganic thickening agents, in particular phyllosilicates such as for example bentonite, particularly smectites, such as montmorillonite or hectorite.

Coloring processes on keratin fibers conventionally take place in the weak acid to alkaline range, preferably in a weak acid to weak alkaline environment. In order to protect the keratin fibers and also the skin, it is not desirable to establish too high a pH, however. The pH of the agents can be between 3 and 11, and preferably between 5 and 8. The pH values are pH values measured at a temperature of 22° C. The alkalizing agents which can be used according to the invention to establish the preferred pH are preferably selected from ammonia, alkanol amines, basic amino acids as well as inorganic alkalizing agents. Preferred inorganic alkalizing agents are magnesium carbonate, sodium hydroxide, potassium hydroxide, sodium silicate and sodium metasilicate. Organic alkalizing agents which can be used according to the invention are preferably selected from monoethanolamine, 2-amino-2-methylpropanol and triethanolamine. The basic amino acids which can be used as the alkalizing agent according to the invention are preferably selected from the group comprising arginine, lysine, ornithine and histidine, particularly preferably arginine. Acidifying agents which can be used to establish the pH are organic acids, such as citric acid, acetic acid, ascorbic acid, benzoic acid, lactic acid, malic acid and maleic acid, as well as mineral acids such as hydrochloric acid, sulfuric acid or phosphoric acid.

It has furthermore proved advantageous for the coloring agents, in particular if they additionally contain hydrogen peroxide, to contain at least one stabilizer or complexing agent. Particularly preferred stabilizers are phenacetin, alkali benzoates (sodium benzoate) and salicylic acid. All prior art complexing agents can moreover be used. Preferred complexing agents according to the invention are nitrogen-containing polycarboxylic acids, in particular EDTA and EDDS, and phosphonates, in particular 1-hydroxyethane-1,1-diphosphonate (HEDP) and/or ethylenediamine tetramethylene phosphonate (EDTMP) and/or diethylenetriamine pentamethylene phosphonate (DTPMP) or the sodium salts thereof.

The agents can moreover contain further active agents, auxiliary substances and additives, such as for example non-ionic polymers, vinylpyrrolidinone/vinyl acrylate copolymers, polyvinylpyrrolidinone, vinylpyrrolidinone/vinyl acetate copolymers, polyethylene glycols and polysiloxanes; additional silicones, such as volatile or non-volatile, straight-chain, branched or cyclic, crosslinked or uncrosslinked polyalkyl siloxanes (such as dimethicones or cyclomethicones), polyaryl siloxanes and/or polyalkylaryl siloxanes, in particular polysiloxanes having organofunctional groups, such as substituted or unsubstituted amines (amodimethicones), carboxyl, alkoxy and/or hydroxyl groups (dimethicone copolyols), linear polysiloxane(A)-polyoxyalkylene(B) block copolymers, grafted silicone polymers; cationic polymers such as quaternized cellulose ethers, polysiloxanes having quaternary groups, dimethyldiallyl ammonium chloride polymers, acrylamide-dimethyldiallyl ammonium chloride copolymers, dimethylaminoethyl methacrylate-vinylpyrrolidinone copolymers quaternized with diethyl sulfate, vinylpyrrolidinone-imidazolinium-methochloride copolymers and quaternized polyvinyl alcohol, in particular Polyquaternium-2, Polyquaternium-4, Polyquaternium-6, Polyquaternium-7, Polyquaternium-10, Polyquaternium-11, Polyquaternium-16, Polyquaternium-24, Polyquaternium-28, Polyquaternium-37, Polyquaternium-44, Polyquaternium-46, Polyquaternium-55, Polyquaternium-67, Polyquaternium-68, Polyquaternium-69 and Polyquaternium-87; zwitterionic and amphoteric polymers, such as in particular Polyquaternium-22 and Polyquaternium-39; structuring agents such as glucose, maleic acid and lactic acid, hair-conditioning compounds such as phospholipids, for example lecithin and cephalins; perfume oils, dimethyl isosorbide and cyclodextrins; active agents to improve the fiber structure, in particular mono-, di- and oligosaccharides such as for example glucose, galactose, fructose, fruit sugars and lactose; dyes for coloring the agent; anti-dandruff active agents such as piroctone olamine, zinc omadine and climbazole; amino acids and oligopeptides; protein hydrolysates of animal and/or plant origin as well as those in the form of their fatty acid condensation products or optionally anionically or cationically modified derivatives thereof; vegetable oils; light stabilizers and UV blockers; active agents such as panthenol, pantothenic acid, pantolactone, allantoin, pyrrolidinone carboxylic acids and salts thereof as well as bisabolol; polyphenols, in particular hydroxycinnamic acids, 6,7-dihydroxy-coumarins, hydroxybenzoic acids, catechins, tannins, leukoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and paraffins; swelling and penetrating substances such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate and PEG-3 distearate; pigments as well as propellants such as propane-butane mixtures, $N_2O$, dimethyl ether, $CO_2$ and air.

A person skilled in the art can select these further substances in accordance with the desired properties of the agents. With regard to further optional components and to the amounts of these components used, reference is expressly made to the relevant manuals known to a person skilled in the art, for example Kh. Schrader, Grundlagen and Rezepturen der Kosmetika, $2^{nd}$ Edition, Hüthig Buch Verlag, Heidelberg, 1989. The additional active agents and auxiliary substances are used in the agents preferably in amounts from 0.0001 to 25 wt. % in each case, in particular from 0.0005 to 15 wt. %, relative to the total weight of the application mixture.

A method for coloring and optionally lightening keratinic fibers, in particular human hair, wherein the agent of the first subject matter of the present technology is applied to the keratin-containing fibers, left on the fibers for 5 to 60 minutes and then rinsed out again with water or washed out with a shampoo, is suitable in particular for the application of the agents. The contact time of the ready-to-use coloring agents is preferably 5 to 45 minutes, in particular 10 to 40 minutes, particularly preferably 15 to 35 minutes. During the contact time of the agent on the fibers it can be advantageous to support the lightening process by supplying heat. Heat can be supplied both from an external heat source, for example hot air from a hot air blower, and also, in particular if the hair lightening process is taking place on a living test subject, from the body temperature of the test subject. In the latter case the section to be lightened is conventionally covered with a hood. A contact phase at room temperature is contemplated as part of the present technology. In particular, the temperature during the contact time is between 20° C. and 40° C., in particular between 25° C. and 38° C. After the end of the contact time the remaining coloring preparation is rinsed out of the hair with water or a cleaning agent. Commercial shampoo can be used in particular as the cleaning agent. In particular if the coloring agent has a carrier having a high surfactant content, then the cleaning agent can be dispensed with and the rinsing process can take place with water.

The agents can be formulated as one-component agents (coloring and lightening agent) or as multi-component agents such as two-component agents or three-component agents, and used accordingly. A separation into multi-component systems is useful in particular where incompatibilities between the ingredients are to be expected or feared; in such systems the agent to be used is prepared by the consumer immediately before use by mixing the components together.

If the agent contains both substantive dyes—as well as optionally additional oxidation dye precursors—and oxidizing agents, they are conveniently packaged separately from one another in order to avoid a premature, undesired reaction and brought into contact only immediately before application.

A coloring method in which the coloring cream and the oxidizing agent are initially kept separate is therefore preferred. The present technology therefore also provides a method for coloring and lightening human hair, wherein a composition on an aqueous basis containing hydrogen peroxide is mixed with an agent according to the invention containing at least one compound of formula (I) to form a homogeneous composition, and this is applied to the hair. The zwitterionic surfactant (b) can in this case be packaged both with the hydrogen peroxide solution and with the compound of formula (I).

In a further embodiment of the present invention agents are therefore preferred which are characterized in that they are produced immediately before application by mixing at least two preparations, wherein the at least two preparations are provided in at least two separately packaged containers, and wherein one container contains an agent (A), which contains in a cosmetic carrier at least one cationic anthraquinone dye of formula (I) and at least one zwitterionic surfactant (b)—as well as optionally additionally oxidation dye precursors, and a further container contains an oxidizing agent preparation (B) containing at least one oxidizing agent.

The formulation of a combination of (a) compounds of general formula (I) with (b) the zwitterionic surfactants is outstandingly suitable for producing intense colors with high brilliance, high shine and a low selectivity in conjunction with an outstanding wash fastness.

Also provided is the use of an agent of the first subject matter of the invention to produce hair dyes having increased shine, an intense color result with improved fastness properties and/or reduced selectivity.

All that has been stated in respect of the agents according to the invention applies with necessary alterations to further preferred embodiments of the methods.

EMBODIMENT EXAMPLES

The following formulations were produced. Unless otherwise specified, the stated quantities are percentages by weight.

| FormulationEexample 1 | wt. % |
| --- | --- |
| Polyquaternium-10 | 0.45 |
| Citric acid monohydrate | 0.70 |
| Timiron Super Silver | 0.20 |
| Cationic Blue 347 | 0.20 |
| Salicylic acid | 0.20 |
| Disodium cocoamphodiacetate | 7.00 |
| Na benzoate | 0.50 |
| Nicotinamide | 0.50 |
| Sodium pyrrolidinone-2-carboxylate | 2.00 |
| Cutina HR | 1.00 |
| PEG-7 glyceryl cocoate | 0.50 |
| Sodium myreth sulfate (2 EO), 70% | 24.0 |
| NaOH, 50% | 0.147 |

-continued

| Formulation Example 1 | wt. % |
|---|---|
| D-Panthenol, 75% | 0.50 |
| Euperlan PK 3000 AM | 2.60 |
| ProSina | 2.0 |
| Sericin H | 0.20 |
| Caramel syrup, 75% | 0.60 |
| Apricot kernel oil | 0.10 |
| PEG-40 hydrogenated castor oil | 0.60 |
| Sodium chloride | 0.20 |
| Antil 141 L | 1.0 |
| Hydrolyzed silk protein | 1.50 |
| Benzophenone-4 | 0.50 |
| Perfume | qs |
| Water | to 100 |

| Formulation example 2 | wt. % |
|---|---|
| Coconut alcohol | 4.00 |
| Cocamidopropyl betaine, 40% | 4.00 |
| Sodium myreth sulfate (2 EO), 27% | 4.00 |
| Laureth-2 | 0.80 |
| Emulgade 1000 NI | 3.00 |
| Methylparaben | 0.15 |
| Propylparaben | 0.19 |
| Polyethylene glycol MG 400 | 3.00 |
| Acid Red 33 | 0.005 |
| N-(2-Hydroxyethyl)-4-methyl-2-nitroaniline (Methyl Yellow) | 0.04 |
| Carbomer [1000-7000 mPas (0.2%)] | 0.50 |
| Monoethanolamine | 0.23 |
| 1,3-Butanediol | 1.00 |
| Water, demineralized | 3.00 |
| Polyquaternium-6 | 0.50 |
| Cationic Blue 347 | 0.20 |
| Perfume | qs |
| Water | to 100 |

Raw Materials Used

| | |
|---|---|
| Cationic Blue 347 | 3-[(4-amino-9,10-dihydro-3-methyl-9,10-dioxo-1-anthracenyl)amino]-N,N,N-trimethyl-1-propanaminium methyl sulfate |
| Emulgade 1000 NI | INCI name: Cetearyl alcohol, Ceteareth-20 (BASF) |
| Timiron Super Silver | INCI name: Mica, Titanium Dioxide (Merck KGaA) |
| Cutina HR | INCI name: Hydrogenated Castor Oil (BASF) |
| Euperlan PK 3000 AM | approx. 43% solid substance; INCI name: Aqua, Glycol Distearate, Glycerin, Laureth-4, Cocamidopropyl Betaine, Formic Acid (BASF) |
| ProSina | INCI name: Aqua, hydrolyzed Keratin (Keratec/Croda) |
| Sericin H | INCI name: Sericin (Pentapharm) |
| Antil 141 L | approx. 40% active substance; INCI name: Propylene Glycol, PEG-55 Propylene Glycol Oleate (Goldschmidt/Evonik) |

What is claimed is:

1. An agent for coloring keratinic fibers comprising, in a cosmetic carrier, (a) at least one compound of formula (I):

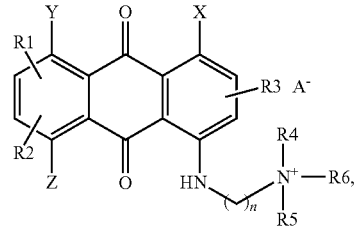

in which:
R1, R2, and R3 each independently of one another denote a hydrogen, a halogen, a nitro group, a cyano group, a carboxyl group, a sulfonic acid group, a hydroxyl group, a C1-C6 acyl amino group, a carboxamide group, a sulfonamide group, a C1-C6 alkyl group, C1-C6 alkoxy group, a C2-C6 alkenyl group, a C2-C6 hydroxyalkyl group or a C1-C6 alkoxy C2-C6 alkyl group;
in which
at least one of the R1, R2 and R3 denotes a halogen, a carboxyl group, a sulfonic acid group, a C1-C6 alkyl group or a C1-C6 alkoxy group;
R4, R5, and R6 each independently of one another denote a C1-C6 alkyl group, a C2-C6 alkenyl group, a C2-C6 hydroxyalkyl group or a C1-C6 alkoxy C2-C6 alkyl group;
X, Y, and Z each independently of one another denote a hydrogen or an N(R7)(R8) group,
wherein
R7 and R8 each independently of one another denote a hydrogen, a C1-C6 alkyl group, a C2-C6 alkenyl group, a C2-C6 hydroxyalkyl group or a C1-C6 alkoxy C2-C6 alkyl group; and at least one of the X, the Y and the Z denote an N(R7)(R8) group;
n denotes an integer from 2 to 6 inclusive; and
A$^-$ denotes a physiologically acceptable anion; and
(b) at least one zwitterionic surfactant.

2. The agent of claim 1, wherein at least one of the R1, R2 and R3 denote a C1-C6 alkyl group.

3. The agent of claim 1, wherein X denotes an NH$_2$ group.

4. The agent of claim 1, wherein the compound of formula (I) comprises a compound according to formula (Ia),

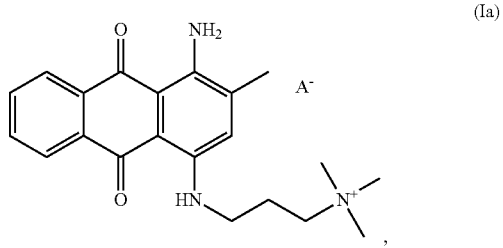

wherein the A$^-$ denotes a physiologically acceptable anion.

5. The agent of claim 1, wherein the compound of formula (I) is present in an amount of from 0.0001 to 5 wt. % of a total weight of the agent.

6. The agent of claim 1, wherein the zwitterionic surfactant comprises at least one of an alkyl amidopropyl dimethyl betaine and an alkyl dimethyl betaine.

7. The agent of claim 1, wherein the zwitterionic surfactant comprises cocamidopropyl betaine.

8. The agent of claim 1, wherein the zwitterionic surfactant is present in an amount of from 0.001 to 15 wt. % of a total weight of the agent.

9. The agent of claim 1, further comprising at least one of a further substantive dye selected from a group comprising: Acid yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue, and tetrabromophenol blue.

10. The agent of claim 1, further comprising at least one of a further substantive dye from a group comprising: Basic Blue 7, Basic Blue 26, Basic Violet 2, Basic Violet 14, Basic Yellow 57, Basic Red 76, Basic Blue 99, Basic Brown 16, Basic Brown 17, Basic Yellow 87, Basic Orange 31, and Basic Red 51.

11. The agent of claim 1, further comprising at least one of a further substantive dye from a group comprising: HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9,1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid, and salts thereof, 2-amino-6-chloro-4-nitrophenol, 4-ethylamino-3-nitrobenzoic acid, and 2-chloro-6-ethylamino-4-nitrophenol.

12. The agent of claim 1, further comprising at least one of a non-ionic surfactant from a group comprising: Laureth-2, Beheneth-10, Ceteareth-12, Trideceth-12, Oleth-16, Ceteareth-20, Ceteareth-30 and Ceteareth-50 as well as PPG-1 Trideceth-6, PEG-7 Oleate, PEG-90 Stearate, PEG-30 Cocoate, Polysorbate-20, Polysorbate-60, Polysorbate-65, Polysorbate-80, Polysorbate-85, Lauryl Glucoside, Decyl Glucoside, and Coco Glucoside.

13. The agent of claim 1, wherein the agent has a pH and the pH is between 5 and 8.

14. A method for coloring human hair, comprising:
   A. applying an agent as recited in claim 1 to the hair;
   B. allowing the agent to act on the hair for a period from 5 to 45 minutes; and
   C. rinsing the hair.

15. An agent for coloring keratinic fibers comprising, in a cosmetic carrier,
(a) at least one compound of formula (I):

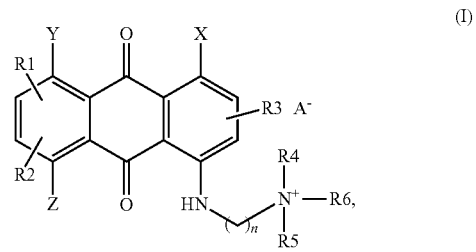

in which:
R1, R2, and R3 each independently of one another denote a hydrogen, a halogen, a nitro group, a cyano group, a carboxyl group, a sulfonic acid group, a hydroxyl group, a C1-C6 acyl amino group, a carboxamide group, a sulfonamide group, a C1-C6 alkyl group, C1-C6 alkoxy group, a C2-C6 alkenyl group, a C2-C6 hydroxyalkyl group or a C1-C6 alkoxy C2-C6 alkyl group;

R4, R5, and R6 each independently of one another denote a C1-C6 alkyl group, a C2-C6 alkenyl group, a C2-C6 hydroxyalkyl group or a C1-C6 alkoxy C2-C6 alkyl group;

X, Y, and Z each independently of one another denote a hydrogen or an N(R7)(R8) group, wherein
R7 and R8, each independently of one another, denote a hydrogen, a C2-C6 alkyl group, a C2-C6 alkenyl group, a C2-C6 hydroxyalkyl group or a C1-C6 alkoxy C2-C6 alkyl group, and at least one of the X, the Y and the Z denote an N(R7)(R8) group;

n denotes an integer from 2 to 6 inclusive; and
A⁻ denotes a physiologically acceptable anion; and
(b) at least one zwitterionic surfactant.

16. The agent of claim 15, wherein X is a $NH_2$.

17. The agent of claim 15, wherein at least one of the R1, R2 and R3 denotes a halogen, a carboxyl group, a sulfonic acid group, a C2-C6 alkyl group or a C1-C6 alkoxy group.

18. The agent of claim 15, wherein n is 2.

19. The agent of claim 15, wherein the compound of formula (I) is present in an amount of from 0.0001 to 0.05 wt. % of a total weight of the agent.

20. The agent of claim 5, wherein the compound of formula (I) is present in an amount of from 0.0001 to 0.05 wt. % of a total weight of the agent.

* * * * *